(12) United States Patent
Bertling

(10) Patent No.: US 6,403,339 B1
(45) Date of Patent: Jun. 11, 2002

(54) METHOD FOR DETECTING A NUCLEOTIDE SEQUENCE

(75) Inventor: Wolf Bertling, Erlangen (DE)

(73) Assignee: November Aktiengesellschaft Gesellschaft fuer Molekulare Medizin, Erlangen (DE)

( * ) Notice: Subject to any disclaimer, the term of this patent is extended or adjusted under 35 U.S.C. 154(b) by 0 days.

(21) Appl. No.: 09/646,575

(22) PCT Filed: Mar. 16, 1999

(86) PCT No.: PCT/DE99/00726

§ 371 (c)(1),
(2), (4) Date: Nov. 16, 2000

(87) PCT Pub. No.: WO99/47701

PCT Pub. Date: Sep. 23, 1999

(30) Foreign Application Priority Data

Mar. 18, 1998 (DE) .......................................... 198 11 731

(51) Int. Cl.[7] .............................................. C12P 19/34
(52) U.S. Cl. ......................... 435/91.2; 435/6; 435/7.1; 435/91.1; 536/23.1; 536/24.3; 536/24.31; 536/24.32; 536/24.33
(58) Field of Search ............................ 435/6, 7.1, 91.1, 435/91.2; 536/23.1, 24.2, 24.31, 24.32, 24.33

(56) References Cited

U.S. PATENT DOCUMENTS

| 5,723,591 A |  | 3/1998 | Livak et al. |  |
| 5,747,251 A | * | 5/1998 | Carson et al. | ................. 435/6 |
| 6,174,670 B1 | * | 1/2001 | Wittwer et al. | ................. 435/6 |

FOREIGN PATENT DOCUMENTS

| WO | WO 92/21780 | 12/1992 |
| WO | WO95/13399 | 5/1995 |
| WO | WO 97/31256 | 8/1997 |
| WO | WO 97/32040 | 9/1997 |

OTHER PUBLICATIONS

"A closed tube format for amplification and detection of DNA based on energy transfer" (Nazarenko et al.), dated 1997.

"A rapid, sensitive and automated method for detection of Salmonella species in foods using AG–9600 AmpliSensor Analyzer" (Chen et al.),.

* cited by examiner

*Primary Examiner*—Jeffrey Siew
(74) *Attorney, Agent, or Firm*—Laurence A. Greenberg; Werner H. Stemer; Gregory L. Mayback

(57) ABSTRACT

A method is disclosed for detecting a nucleotide sequence by a polymerase chain reaction, the nucleotide sequence is a constituent of a double-stranded nucleic acid molecule which is in solution and formed of a strand and a counter-strand. A first primer is added to the solution and is complementary to a first segment of the strand located at the 5'-terminus of a central segment. A second primer is added and is complementary to a 5'-terminal second segment of the counter-strand. The solution is brought into contact with a third primer whose 5'-terminal end is bound to a solid phase. The third primer is complementary to the central segment of the strand containing the nucleotide sequence. A reaction vessel is closed which contains the solution. The solution is repeatedly heated and cooled and the nucleic acid molecule is detected in the closed reaction vessel.

13 Claims, 2 Drawing Sheets

METHOD FOR DETECTING A NUCLEOTIDE SEQUENCE

BACKGROUND OF THE INVENTION

Field of the Invention

The invention relates to a method for detecting a nucleotide sequence. It furthermore relates to a kit for carrying out the method.

Such a method is known by the term "polymerase chain reaction" (PCR). PCR is suitable for the generation of large amounts of a desired DNA sequence. To carry out the method, two synthetic oligonucleotide primers which are complementary to sections on a strand and on a counter-strand which flank the desired DNA sequence, are added to a solution comprising the sample. After amplification, the desired DNA sequence can be detected by addition of detection reagents, for example by means of a color reaction or electrophoresis.

The known PCR method requires a long reaction time, owing to necessary diffusions in the solution. Moreover, the detection of the PCR product formed, for example by means of color reaction or electrophoresis, is time consuming. Moreover, it is necessary, for detection, to open the reaction batch comprising the multiplied products. This constitutes a risk of contamination. Finally, the sensitivity of the known method is insufficient for certain applications.

WO 94/02636 describes a method in which a first primer bound to a solid phase is brought into contact and hybridized with a sample comprising a nucleotide sequence. Thereupon, the sample container is opened, and the sample is treated with a second primer, whereupon the nucleotide sequence hybridizes. The second primer is labeled. It accumulates on the solid phase, where the label can be observed. Furthermore, it is known from WO 94/02636 to carry out a polymerase chain reaction using three primers in solution, the solution being brought into contact successively with the primers.

The disadvantage of the methods disclosed in WO 94/02636 is that the reaction vessel must be opened in order to bring the sample into contact with the second and, if appropriate, the third primer. This may result in contaminations.

WO 96/26291 describes a method for distinguishing between several alternative DNA sequences. In this method, a first and a second primer are bound to a solid phase. A third primer is in solution. This method is only suitable for distinguishing between the presence of alternative DNA sequences, but not for detecting a particular nucleotide sequence. In the PCR, only two primers are included in the reaction, one of which is bound to a solid phase. This primer shows a low degree of mobility and accessibility. The method is less suited for PCR than when free primers are present.

A method for the specific detection of DNA sequences is known from Chemical Abstracts 126: 70853z (1997) re: chapture [sic] PCR amplification with single-sided specifity across mutation break-points; Lagerstroem-Fermer, Maria et al; Lab. Protoc. Mutat. Detect. 1996, 183–188. In this method, the DNA sequences to be detected are first amplified and then bound to a solid phase. In subsequent steps, the DNA sequence to be detected is detected by further PCRs. In this method, the DNA sequence to be detected is immobilized on the solid phase by binding.

The use of synthetic residues in primers which cannot be replicated is known from Chemical Abstracts 120: 155091a (1994): Incorporation on nonbase residues into synthetic oligonucleotides and their use in the PCR; Gade et al.; Genet. Anal.: Tech. Appl. 1993, 10(2), 61-5. In the PCR, double-stranded DNA is produced by the polymerase until the latter encounters such a synthetic residue. From this position on, the DNA strand remains single-stranded. The single-stranded DNA sequence is capable, without previous denaturation, of hybridizing with a complementary, further DNA bound to a solid phase.

The fact that a fluorescence energy transfer is possible between fluorogenic groups bound to oligonucleotides when these fluorogenic groups are fixed at defined intervals by a hybridization is known from Cardullo R. A. et al: Detection of nucleic acid hybridisation by nonradiative fluorescence resonance 15 energy transfer; Proc. Natl. Acad. Sci. USA 85 (1988) 8790–8794.

A method for detecting specific DNA in which the sample is initially subjected to a first amplification by means of PCR is disclosed in WO 90/11369. Thereupon, the sample is transferred into another reaction vessel, where it is brought into contact with a second primer, which is bound to a solid phase. A second amplification by means of PCR takes place. Again, this method suffers the disadvantage of a risk of contamination when transferring the sample from the first into the second reaction vessel.

The object of the invention is to eliminate the disadvantages of the prior art. In particular, it is intended to state a rapid method for detecting a nucleotide sequence with a reduced risk of contamination.

SUMMARY OF THE INVENTION

This object is achieved within the scope of the invention by a method for detecting a nucleotide sequence by means of polymerase chain reaction, where the nucleotide sequence is a constituent of a double-strained nucleic acid molecule which is in solution and which is comprised of a strand (S) and a counter-strand (G), the method comprising the following steps:

a) adding a first primer to the solution, where the first primer is complementary to a first segment of the strand located at the 5'-terminus of a central segment, and a second primer, where the second primer is complementary to a 5'-terminal second segment of the counter-strand, b) bringing the solution into contact with a third primer whose 5'-terminal end is bound to a solid phase, where the third primer is complementary to the central segment of the strand comprising the nucleotide sequence, c) closing a reaction vessel which contains the solution, d) repeatedly heating and cooling the solution with the following steps:
  d1) heating to 92° C.–100° C.
  d2) cooling to 40° C.–600° C.
  d3) heating to 72° C.–75° C. and e) detecting the nucleic acid molecule during or after step lit. [sic] d) with a closed reaction vessel.

This concentrates the desired nucleotide sequence on the solid phase. The reaction time required is shortened and the sensitivity improved.

The third primer is advantageously a DNA molecule or a PNA/DNA chimera.

The solid phase is a polymer, preferably an electrically conductive polymer, which may comprise a polycarbonate, trimethylthiophene, triaminobenzene and/or a polycarbene and/or carbon fibers. The solid phase is expediently a microtiter plate in whose well the third primer may be bound covalently or by means of biotin.

In an especially advantageous embodiment feature, an interaction allowing a nonradiative or direct energy transfer between a first and a second fluorophoric molecule is generated or removed when the nucleotide sequence is present. The first fluorophoric molecule may be bound to the solid phase, or else the first fluorophoric molecule is bound to the solid phase via the third primer.

A particularly simple variant consists in the third primer having a hairpin loop and the first fluorophoric molecule being bound to a first loop segment and the second fluorophoric molecule opposite to a second loop segment at a distance which allows the interaction to take place. The interaction can be removed by hybridization with a counter-strand which is complementary to the third primer or by a synthesis taking place on the third primer. In this context, the second fluorophoric molecule may be bound to the second primer. The abovementioned features allow simple and automatable detection of the nucleic acid molecule as early as during the PCR.

The invention furthermore provides a kit for carrying out the method according to the invention, comprising, as first component, a first primer and as second component a second primer, and also a third primer whose 5'-terminal end is bound to a solid phase.

The solid phase is expediently a microtiter plate. As further components, the kit may comprise the buffers required for carrying out the polymerase chain reaction, the deoxynucleotide triphosphates required for multiplying the nucleotide sequence, and the polymerase required for carrying out the polymerase chain reaction, preferably a Taq polymerase.

The first primer and the second primer and also the further components may be present in the lyophilized state. Thus, a reaction may be started by adding the solution comprising the nucleotide sequence. Alternatively the first and the second and/or the further components may be coated with wax. This allows the reaction to be started by heating the solution comprising the nucleotide sequence and the coated components.

Advantageous embodiments of the invention are illustrated in greater detail hereinbelow with reference to the in the drawing [sic]. The figures show:

DESCRIPTION OF THE PREFERRED EMBODIMENT

Figure 1:
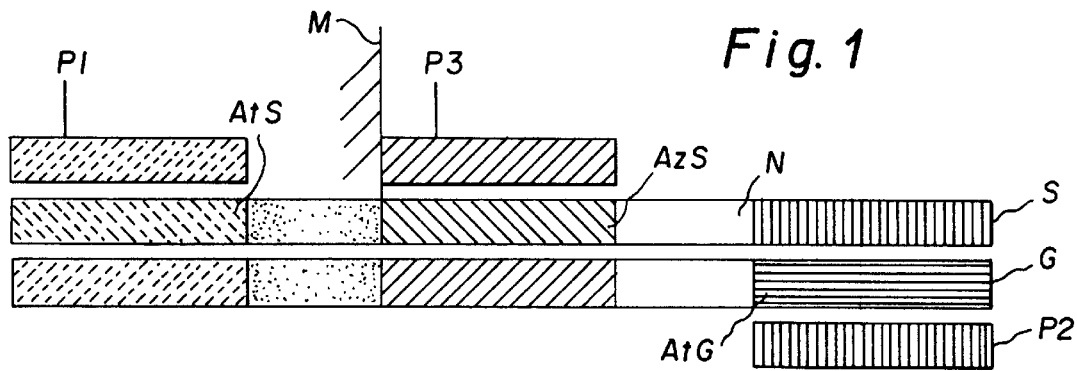
FIG. 1 the pairing of a strand and a counter-strand with the primers.

FIG. 1 shows a strand S comprising the desired nucleotide sequence N, and its complementary counter-strand G. A first primer P1 hybridizes with a 5'-terminal segment AtS of the strand S and a second primer P2 with a 5'-terminal segment AtG of the counter-strand G. A central segment AzS of the strand S hybridizes with a third primer P3 whose 5'-terminal end is bound to a solid phase M. The third primer P3 is a DNA or PNA/DNA chimera. Here, the solid phase M consists of an electrically conductive polycarbonate. Owing to its electrical conductivity, the solid phase M may also be used as a resistance heating element.

Figure 2:
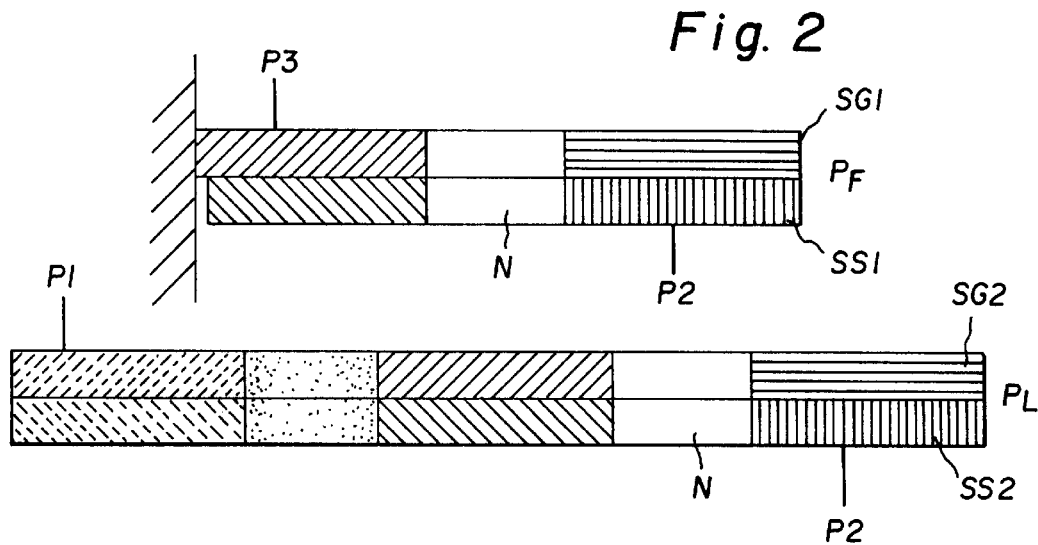
FIG. 2 the products formed after carrying out the PCR.

FIG. 2 shows the products formed after carrying out the PCR method described hereinbelow. A short product $P_F$ is bound to the solid phase M via the third primer P3. The third primer P3 is a component of a synthesis counter-strand SG1. Paired with the synthesis counter-strand SG1 is a synthesis strand SS1 comprising the nucleotide sequence N and the second primer P2. A long product $P_L$ in the solution comprises the first primer P1 in the synthesis counter-strand SG2 and the second primer P2 and also the nucleotide sequence N in the synthesis strand SS2.

Figure 3:
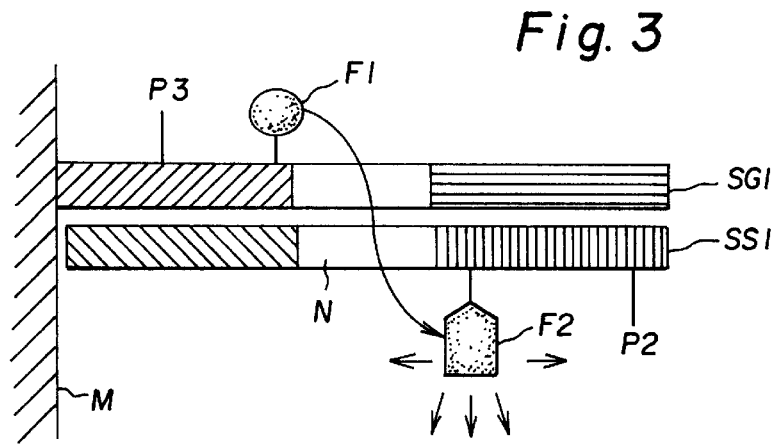
FIG. 3 a first possibility of detecting the nucleotide sequence.

FIG. 3 shows a first possibility of detecting the nucleotide sequence N. A first fluorophoric molecule F1 is bound to the third primer P3 and a second fluorophoric molecule F2 to the second primer. The first fluorophoric molecule F1 is a donor group and the second fluorophoric molecule F2 a corresponding acceptor group. When pairing of the strand SS1 with the counter-strand SG1 takes place, the distance between the donor and the acceptor group is approximately 30 to 60 Å. In this state, the so-called Förster effect leads to the generation of interactions between the donor group and the acceptor group. The table hereinbelow shows suitable donor/acceptor compounds:

| Donor | Acceptor |
| --- | --- |
| Fluorescein | Tetramethylrhodamine |
| IAEDANS (= 5-((((2-iodoacyl) - amino) ethyl) amino) naphthalene -1-sulfonic acid | Fluorescein |
| EDANS (= 5-((2-aminomethyl) - amino) naphthalene-1-sulfonic acid | DABCYL (4-dimethylamino-azobenzene-4'-sulfonyl chloride |
| BODIPY FL | BODIPY FL |
| Fluorescein | Fluorescein |

Suitable quencher/fluorophore pairs can be seen from the table which follows:

| Quencher | Fluorophore |
| --- | --- |
| DABCYL | Coumarin |
| DABCYL | EDANS |
| DABCYL | Fluorescein |
| DABCYL | Lucifer Yellow |
| DABCYL | Bodipy |
| DABCYL | Eosin |
| DABCYL | Tetramethylrhodamine |
| DABCYL | Texas Red |
| DABCYL | Erythrosin |

Figure 4:
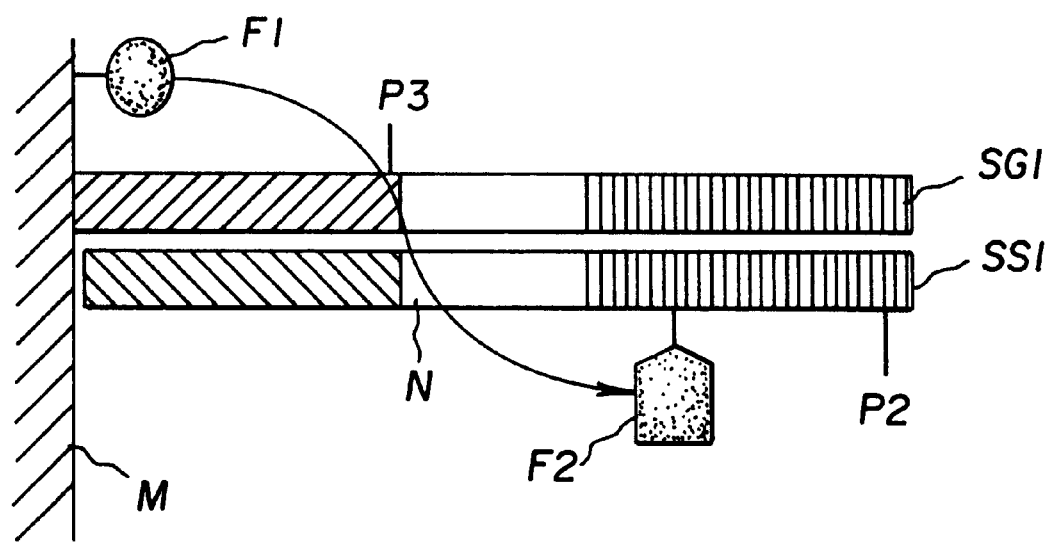
FIG. 4 a second possibility of detecting the nucleotide sequence.

FIG. 4 shows a further possibility of detecting the nucleotide sequence. In contrast to the possibility shown in FIG. 3 the first fluorophoric molecule F1 is bound directly to the solid phase M in the vicinity of the third primer P3.

To carry out the method, it is advantageous to use a 96-well microtiter plate made of polycarbonate or polypropylene which may comprise a conductive polymer component such as, for example, polycarbene, trimethylthiophene and/or triaminobenzene and/or carbon fibers. The third primer P3 is bound to the cavities. The microtiter plate is part of an electrical circuit and is a resistant heating element.

The samples and the further components required for carrying out the PCR are pipetted into the wells. These comprise, in particular, the first primer P1 and the second primer P2 with a second fluorophoric molecule F2 bound thereto. A target DNA localized in the sample is denatured by raising the temperature to 95°, i.e. separated into the strand S and the corresponding counter-strand G.

Then, the temperature is reduced to 40 to 60°. The central segment AzS of the strand S binds to the third primer P3 and the further 5'-terminal segment AtS of the strand S to the first primer P1. The second primer P2 binds to the 5'-terminal segment of the counter-strand G. Then, the sequence segments missing in each case are subsequently synthesized at 72° C. by means of a Taq DNA polymerase. The temperature is then raised to 95° C. so that the synthesis strands comprising the fluorophoric molecules F1, F2 are present as single strands, viz. as the synthesis strand SS1 and the synthesis counter-strand SG1. The temperature is reduced to 50 to 60°. The synthesis strand SS1 and the synthesis counter-strand SG1, which is bound to the solid phase M, pair so that the first fluorophoric molecule F1 and the second fluorophoric molecule F2 are present at a segment [sic] of 30 to 60 Å. This is shown schematically in FIG. 3.

Upon excitation of the first fluorophoric molecule F1, which acts as the donor, a nonradiative energy transfer to the second fluorophoric molecule F2, which acts as the acceptor, takes place. This causes an increased fluorescence to be observed on the second fluorophoric molecule F2. The fluorescence can be detected by means of a fluorometer. For evaluation, the detection data are transmitted to a data-processing system.

Then, the next PCR cycle is initiated by raising the temperature. This results in a further multiplication of the synthesis strand SS1 and the synthesis counter-strand SG1. Both the nucleotide sequence N contained in the sample and the resulting PCR product $P_F$ act as template for the PCR product $P_F$.

The change in fluorescence intensity over the number of PCR cycles is a measure for the starting concentration of the nucleotide sequence. The more nucleotide sequence the sample contains, the more rapidly the fluorescence intensity increases.

In the further detection possibility shown in FIG. 4, the first fluorophoric molecule F1 is bound directly to the solid phase M. The third primer P3 is bound to the solid phase M in the vicinity of the first fluorophoric molecule F1. After the pairing of the synthesis strand SS1 with the synthesis counter-strand SG1 has taken place, excitation results in a nonradiative or direct energy transfer from the first fluorophoric molecule F1 (donor) to the second fluorophoric molecule F2 (acceptor), where fluorescence occurs.

The third primer P3 may also have a hairpin loop, where the first fluorophoric molecule F1 is bound to a first loop segment and the second fluorophoric molecule F2 to an opposite second loop segment at a distance which allows the interaction to take place. In this case, the first fluorophoric molecule F1 and the second fluorophoric molecule F2 are preferably chosen in such a way that the interaction generated when the hairpin loop is closed causes the fluorescence to be quenched. Hybridization with a counter-strand G which is complementary to the third primer P3, or a synthesis which takes place on the third primer P3, opens the hairpin loop. The interaction between the first fluorophoric molecule F1 and the second fluorophoric molecule F2 is abolished. Excitation of the fluorophoric molecules results in fluorescence.

Instead of utilizing fluorescence effects, the nucleotide sequence N may also be detected using labeled primers. To this end, it is possible, for example, for the second primer P2 to be biotinylated and to be detected by means of a color reaction by means of a via a [sic] streptavidin- or avidin-coupled enzyme on the solid phase. Likewise, the second primer P2 may be labeled with an antibody which is detectable in a color reaction by means of a further, enzyme-labeled antibody. It is also conceivable to label the second primer P2 with digoxigenin and then to detect it in a color reaction via enzyme-labeled anti-digoxigenin antibodies.

It is furthermore possible for the nucleotide sequence N to be detected using labeled nucleotides. To this end, some of the nucleotides may be biotinylated and can be detected by means of a color reaction by means of a streptavidin- or avidin-coupled enzyme on the solid phase. Some of the nucleotides may be labeled with digoxigenin and can be detected in a color reaction via enzyme-labeled anti-digoxigenin-antibodies. Some of the nucleotides may also be fluorescence-labeled, and the incorporation can be detected via a fluorometer.

An increase in layer density is caused the [sic] by the formation of the PCR products $P_F$ on the solid phase M. This increase in layer density can be measured by plasmon resonance, laser-optical methods, or the change in electrical properties.

| Reference list | |
|---|---|
| P1 | first primer |
| P2 | second primer |
| P3 | third primer |
| M | solid phase |
| N | nucleotide sequence |
| S | strand |
| G | counter-strand |
| SS1 | synthesis strand |
| SG1 | synthesis counter-strand |
| SS2 | further synthesis strand |
| SG2 | further synthesis counter-strand |
| $P_F$ | short PCR product |
| $P_L$ | long PCR product |
| F1 | first fluorophoric molecule |
| F2 | second fluorophoric molecule |
| AzS | central strand segment |
| AtS | 5'-terminal strand segment |
| AtG | 5'-terminal counter-strand segment |

What is claimed is:

1. A method for detecting a nucleotide sequence by means of polymerase chain reaction, wherein the nucleotide sequence is a constituent of a double-stranded nucleic acid molecule which is in solution and which is comprised of a strand and a counter-strand, the method which comprises the following steps:

adding a first primer to the solution, wherein the first primer is complementary to a first segment of the strand located at a 3'-terminus of a central segment, and adding a second primer, therein the second primer is complementary to a 3'-terminus of the central segment of the counter-strand;

contacting the solution with a third primer whose 5'-terminal end is bound to a solid phase, wherein the third primer is complementary to the central segment of the strand comprising the nucleotide sequence;

closing a reaction vessel containing the solution;

repeatedly heating and cooling the solution with the following steps:

heating to 92° C.–100° C.;

cooling to 40° C.–60° C.;

heating to 72° C.–75° C;

and detecting the nucleic acid molecule during or after the heating and cooling step in a closed reaction vessel by forming or removing an interaction allowing a nonradiative energy transfer or a direct energy transfer between a first and a second fluorophoric molecule if the nucleic sequence is present, wherein the first fluorophoric molecule is bound to the solid phase or to the third primer, and the second fluorophoric molecule is bound to the second primer.

2. The method according to claim 1, wherein the third primer is selected from the group consisting of a DNA molecule and a PNA/DNA chimera.

3. The method according to claim 1, wherein the solid phase is a plastic material.

4. The method according to claim 3, wherein the plastic material is electrically conductive.

5. The method according to claim 3, wherein the plastic material contains at least one component selected from the group consisting of a polycarbonate, trimethylthiophene, triaminobenzene, a polycarbene, and carbon fibers.

6. The method according to claim 1, wherein the solid phase is a microtiter plate having a well and said third primer is covalently bound in said well.

7. The method according to claim 1, wherein the solid phase is a microtiter plate having a well and said third primer is bound in said well by biotin.

8. The method according to claim 1, which comprises forming an interaction allowing a nonradiative or direct energy transfer between a first and a second fluorophoric molecule if the nucleotide sequence is present.

9. The method according to claim 1, wherein the first fluorophoric molecule is bound to the solid phase.

10. The method according to claim 9, wherein the first fluorophoric molecule is bound to the solid phase via the third primer.

11. The method according to claim 1, which comprises removing an interaction allowing a nonradiative or direct energy transfer between a first and a second fluorophoric molecule if the nucleotide sequence is present.

12. The method according to claim 1, which comprises performing the nonradiative energy transfer between the first and the second fluorophoric molecule if the nucleotide sequence is present.

13. The method according to claim 1, which comprises performing the direct energy transfer between the first and the second fluorophoric molecule if the nucleotide sequence is present.

* * * * *